United States Patent [19]
Ellis

[11] Patent Number: 4,655,207
[45] Date of Patent: Apr. 7, 1987

[54] BODY RESTRAINT

[76] Inventor: Thomas B. Ellis, 3015 Weymouth, Apartment 106, Durham, N.C. 27707

[21] Appl. No.: 789,742

[22] Filed: Oct. 21, 1985

[51] Int. Cl.$^4$ .......................... A61F 5/37; A61G 7/06
[52] U.S. Cl. .................................................. 128/135
[58] Field of Search ................ 269/328; 128/133, 134, 128/135; 5/508, 61, 424

[56] References Cited

U.S. PATENT DOCUMENTS

| | | | |
|---|---|---|---|
| 264,678 | 9/1882 | Farrar | 128/135 |
| D. 275,230 | 8/1984 | Hubbard et al. | 128/133 X |
| 852,638 | 5/1907 | Thomas | 128/135 |
| 3,236,234 | 2/1966 | Buckley | 128/134 |
| 3,276,431 | 10/1966 | Murcott | 128/134 X |
| 3,485,241 | 12/1969 | Polley | 128/135 |
| 3,512,189 | 5/1970 | Swanson | 128/134 X |
| 3,672,364 | 6/1972 | Rankin | 128/134 |
| 4,132,230 | 1/1979 | Ladd | 128/134 |
| 4,180,879 | 1/1980 | Mann | 128/134 X |
| 4,488,544 | 12/1984 | Triunfol | 128/134 |
| 4,536,903 | 8/1985 | Parker | 128/134 X |

FOREIGN PATENT DOCUMENTS 3015371 10/1981 Fed. Rep. of Germany ...... 128/135

OTHER PUBLICATIONS

Patient Safety Aids, J. T. Posey Company, p. 9, 1985.

*Primary Examiner*—S. J. Richter
*Attorney, Agent, or Firm*—Richard E. Jenkins

[57] ABSTRACT

A restraint for holding a person in a side-lying position on a bed and comprising a flexible main section with one or more arm members extending therefrom and further including fastening straps for engaging the bed. The restraint is adapted so as to be quickly and easily attached to and removed from a person being restrained in the side-lying position so as to accommodate usage by a singular health care provider.

14 Claims, 3 Drawing Figures

BODY RESTRAINT

DESCRIPTION

1. Technical Field

This invention relates generally to patient restraint devices used in the health field. Even more specifically, the invention relates to an improved body restraint which is particularly adapted for ease of use in holding a side-lying patient in the side-lying position.

2. Background Art

Body restraints or positioning devices are presently used in the health field for a variety of purposes. For example, Mann U.S. Pat. No. 4,180,879 shows a body positioner for turning and holding a person lying on a bed comprising a shaped body sheet which extends entirely around the torso of the patient and is secured to the bed rail.

Swanson U.S. Pat. No. 3,512,189 describes a patient aid device for assisting bed patients in hospital settings, including maintaining the patient on his side. The device includes a rigid L-shaped support which is secured to the mattress of the patient's bed.

Hubbard et al. U.S. Design Pat. No. 275,230 shows an ornamental design for a body restrainer. The restrainer comprises a portion fitted about the upper body which is secured by straps to a bed in which the restrained person is lying.

Buckley U.S. Pat. No. 3,236,234, Ladd U.S. Pat. No. 4,132,230, Murcott U.S. Pat. No. 3,276,431 and Triunfol U.S. Pat. No. 4,488,544 also disclose restraint garments adapted to be secured to the chest or torso of a patient in order to facilitate confining the subject to a bed. All of these restraints substantially circumscribe the body and are time consuming to secure to and remove from a patient confined to a bed.

DISCLOSURE OF THE INVENTION

In hospitals, nursing homes, doctors' offices and home settings, it is many times desirable to maintain a patient in a side-lying position for either a short period or a prolonged period of time. Typically, a temporary use of a restraint in order to hold a patient in the side-lying position would be required while the patient's bed is being changed, custodial care is provided, specific treatments are administered (e.g., barium enema, proctoscopic examination, colonoscopic examination) and to provide intermittent pressure relief. A restraint may be applied to a patient for longer term usages such as would be required by any totally dependent person, a surgical patient still under the effect of anesthesia, patients who are medically incapacitated or unconscious, patients with severe respiratory or cardiac disease who must be prevented from any significant exertion, and the like.

The restraint of the present invention, in contrast to the prior art restraint devices, provides for a restraint which can be applied and removed by a singular health care provider. Moreover, the restraint is constructed so as not to substantially circumscribe the entire body but merely to be draped over the uppermost side of a side-lying patient. While securely restraining the patient in the side-lying position on a bed, the device is merely draped over the patient and therefore may be removed by a singular health care provider by merely lifting it off the patient. It should be further appreciated that the restraint is secured at one end to a bed rail or other suitable location and that a portion of the body contact side of the restraint comprises a special non-skid material to facilitate securement of the patient in the side-lying position when the restraint is draped on the patient.

An object of the invention is to provide an improved restraint which can readily be used to support a patient in the side-lying position in a bed.

Another object of the invention is to provide an improved restraint for side-lying patients which can be utilized by a singular health care provider to secure a patient in the side-lying position.

A further object of the invention is to provide a restraint for side-lying patients which may be quickly secured to and removed from a side-lying patient.

Still another object of the restraint is to provide a restraint for a side-lying patient which is more comfortable to the patient than patient restraining devices known heretofore.

BRIEF DESCRIPTION OF THE DRAWINGS

These and other aspects of the invention will be more fully understood from the following detailed description and an explanation of the accompanying drawings in which.

BEST MODE FOR CARRYING OUT THE INVENTION

Figure 1:
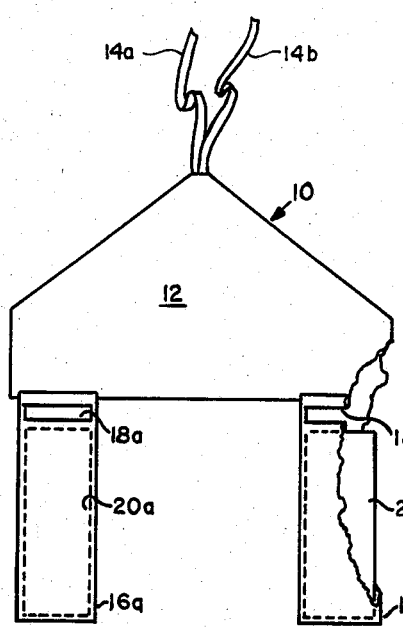
FIG. 1 is a top plan view of the restraint with parts broken away for clarity.

Referring first to FIG. 1, reference numeral 10 designates a body restraint 10 which is constructed so as to be draped over a side-lying patient in a bed in order to maintain the patient in that position and which is further adapted to be easily placed upon and removed from the patient. Restraint 10 includes a triangular main section 12 which is most suitably of a two-ply canvas construction. Fastening straps 14a, 14b are sewn to the top of main section 12. Restraint 10 further includes arms 16a, 16b which are each secured at one end thereof to main section 12 by suitable means such as sewing. It should be appreciated that arms 16a, 16b are constructed of canvas and each define an enclosed pocket space therein. Access to the pocket space within arms 16a, 16b is available through access openings 18a, 18b in the uppermost portion of arms 16a, 16b. Arms 16a, 16b of restraint 10 are therefore adapted to slidably receive weight members 20a, 20b therein through openings 18a, 18b. Weight members 20a, 20b are preferably envelopes of packets containing a suitable substance for providing enhanced weight to arms 16a, 16b such as water, sand or the like. It is believed that the additional weight provided to arms 16a, 16b by weight members 20a, 20b is important to help a sure proper functioning of the subject invention.

Figure 2:
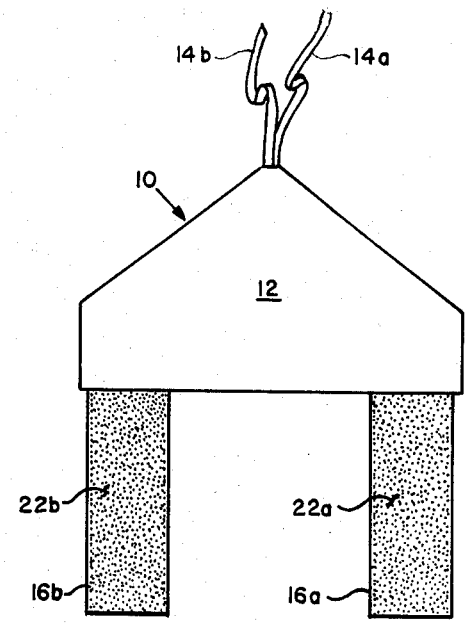
FIG. 2 is a bottom plan view of the restraint.

Referring now to FIG. 2, it should be fully appreciated that this figure depicts the patient contact side of restraint 10 whereas FIG. 1 depicts the top side of restraint device 10. In this view it can be seen that arms 16a, 16b are covered on the patient contact side with non-skid surface material 22a, 22b. The non-skid surface material may most suitably be sewn to the patient contact side of arms 16a, 16b and is commercially available under the trade name DYCEM.

Figure 3:
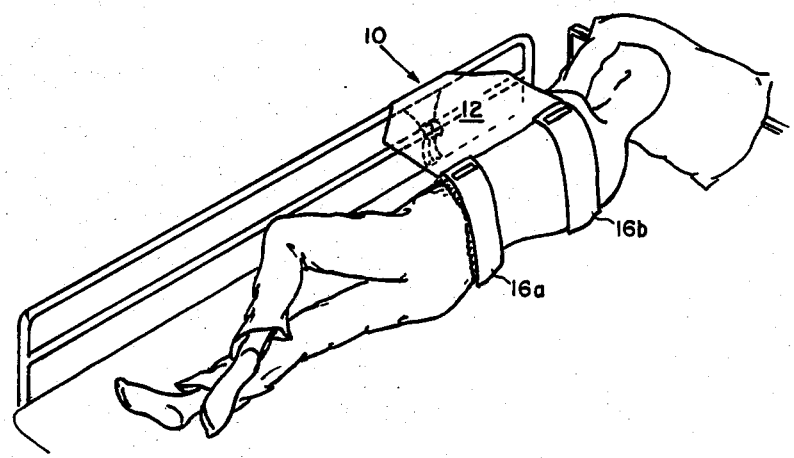
FIG. 3 shows a restraint supporting a patient in a side-lying position.

In operation, a patient is rolled into a side-lying position facing the bed rail by a health care provider (see FIG. 3). Next, the health care provider drapes restraint 10 over the patient with arms 16a, 16b extending generally downwardly across the patient's back. The main section 12 is then pulled by the health care provider laterally toward the bed rail and secured thereto by fastening straps 14a, 14b. It can now be fully appreciated how simply the patient may be restrained in the side-lying position by the use of the device of the present invention. Moreover, in order to temporarily remove the restraint from the patient, it is necessary only to remove arms 16a, 16b from the patient and the patient will be completely unencumbered by the restraint. This is in contrast to previously known restraint devices which are time consuming to secure and remove from the patient and which typically are quite cumbersome and uncomfortable to the patient.

While the instant invention has been shown and described herein in what is conceived to be the most practical and preferred embodiment, it is recognized that departures may be made therefrom within the scope of the invention, which is therefore not to be limited to the details disclosed herein but is to be accorded the full scope of the claims so as to embrace any and all equivalent apparatus and articles.

What is claimed is:

1. A restraint for holding a person in a side-lying position on a bed, said restraint comprising a flexible main section, at least one flexible weighted arm member depending from said flexible main section, and means affixed to said main section for securing said restraint to the bed, whereby said restraint may be placed over the uppermost side of the person in the side-lying position with said at least one flexible weighted arm member extending generally across the back of the person and the restraint secured with said securement means to the bed.

2. A restraint according to claim 1 wherein said means for securing comprises a plurality of straps extending from said flexible main section.

3. A restraint according to claim 1 wherein the body contact side of said arm member comprises a non-skid surface material.

4. A restraint according to claim 1 wherein said restraint includes two spaced-apart arm members.

5. A restraint for holding a person in a side-lying position on a bed, said restraint comprising a flexible sheet main section, a plurality of weighted arm members depending from said main section, and strap means affixed to said main section for securing said restraint to the bed, whereby said restraint may be placed over the uppermost side of the person in the side-lying position with said weighted arm members extending generally downwardly across the back of the person and the restraint secured with said strap means to the bed.

6. A restraint according to claim 5 wherein the body contact side of said arm members comprises a non-skid surface material.

7. A restraint according to claim 6 wherein said non-skid surface material is DYCEM.

8. A restraint according to claim 5 wherein said main section is canvas.

9. A restraint according to claim 5 wherein said strap means comprises two straps.

10. A restraint according to claim 5 wherein said weighted arm members each includes a fluid weight element.

11. A restraint according to claim 10 wherein each of said arm members contains a pocket for receiving the fluid weight element therein.

12. A restraint for holding a person in a side-lying position on a bed, said restraint comprising a flexible sheet main section, two weighted arm members depending from said main section and having a non-skid surface material on the body side thereof, and strap means affixed to said main section for securing said restraint to the bed, whereby said restraint may be placed over the uppermost side of the person in the side-lying position with said weighted arm members extending generally downwardly across the back of the person and the restraint secured with said strap means to the bed.

13. A restraint according to claim 12 wherein said non-skid surface material is DYCEM.

14. A restraint according to claim 12 wherein said weighted arm members each includes a fluid weight element slideably received by a pocket therein.

* * * * *